United States Patent [19]

Freenor, III

[11] 4,244,959
[45] Jan. 13, 1981

[54] FUNGICIDAL O-ACYL (ALPHA-NITRO-FORMALDOXIME) AND (ALPHA-HALO-FORMALDOXIME)-PYRIDINES

[75] Inventor: Francis J. Freenor, III, Richmond, Calif.

[73] Assignee: Chevron Research Company, San Francisco, Calif.

[21] Appl. No.: 54,217

[22] Filed: Jul. 2, 1979

[51] Int. Cl.³ .................... A01N 43/40; C07D 213/44
[52] U.S. Cl. .................................. 424/263; 546/334; 546/335
[58] Field of Search ................... 546/335; 424/263

[56] References Cited

U.S. PATENT DOCUMENTS

| | | | |
|---|---|---|---|
| 3,409,625 | 11/1968 | Ishikawa et al. | 546/335 |
| 3,903,113 | 9/1975 | Bradshaw et al. | 546/335 |

FOREIGN PATENT DOCUMENTS

| | | |
|---|---|---|
| 2217180 | 10/1972 | Fed. Rep. of Germany. |
| 2361504 | 5/1974 | Fed. Rep. of Germany. |
| 46-6766 | 2/1971 | Japan ...................... 546/335 |
| 50-15844 | 6/1975 | Japan. |
| 487884 | 10/1975 | U.S.S.R. ................... 546/335 |

OTHER PUBLICATIONS

Biffin et al., Tetrahedron Letters, 1971, pp. 3849–3852.
Schnekenburger et al., Arch. Pharm., 195, 308(1), 33–41.

*Primary Examiner*—Ethel G. Love
*Attorney, Agent, or Firm*—D. A. Newell; T. G. DeJonghe; R. J. Suyat

[57] ABSTRACT

Novel O-acyl (alpha-halo-formaldoxime)-pyridines are represented by the formula:

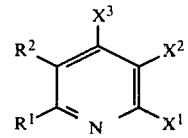

wherein $R^1$ and $R^2$ are individually hydrogen or alkyl of 1 to 4 carbon atoms; $X^1$, $X^2$ and $X^3$ are individually hydrogen, alkyl of 1 to 4 carbon atoms or the group

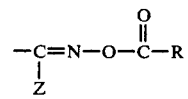

wherein Z is halo or nitro and R is alkyl alkenyl, alkynyl alkoxy, alkoxyalkyl, halovinyl, phenyl, phenyl substituted with halo, alkyl, alkoxy or nitro, amino, alkylamino, or dialkylamine; with the proviso that only one of $X^1$, $X^2$ or $X^3$ is

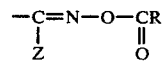

These formaldoxime pyridines, their acid addition salts and their N-oxides are useful as fungicides.

15 Claims, No Drawings

FUNGICIDAL O-ACYL (ALPHA-NITRO-FORMALDOXIME) AND (ALPHA-HALO-FORMALDOXIME)-PYRIDINES

DESCRIPTION OF THE PRIOR ART

U.S. Pat. No. 4,110,104, issued Aug. 29, 1978, discloses herbicidal aminohalopyridyloxy acids and derivatives thereof.

Japanese Pat. No. 5,015,844, published June 27, 1967, discloses agricultural bactericidal 3,5-dichloro-4-alkoxy-(alpha-chloro)benzaldoximes.

Biffin et al, *Tetrahedron Letters*, 1971, pages 3849–52, disclose (alpha-chloro-formaldoxime)pyridines in dehydrochlorination studies forming nitrile N-oxides.

German Offenlegungsschrift No. 2,217,180, published Oct. 26, 1972, discloses pharmaceutically useful (alpha-aralkylthio-formaldoxime)pyridines.

German Offenelgungsschrift No. 2,361,504, published May 22, 1974, discloses 2-aldoxime pyridine quaternary salts as plant growth regulators.

SUMMARY OF THE INVENTION

It has now been found that O-acyl (alpha-halo-formaldoxime) pyridines, their salts and N-oxides are useful fungicides. It has been found that activity is particularly sensitive to the nature of the O-acyl group. The compounds of the invention are particularly useful against fungal species tomato late blight (*Phytophthora infestans*), celery late blight (*Septoria apii*), grape downy mildew (*Plasmopara viticola*), bean powdery mildew (*Erysiphe polygoni*), *Fusarium moniloforma* and *Aspergillus niger*.

DESCRIPTION OF THE INVENTION

The pyridine compounds of the invention are represented by the formula (I)

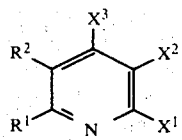

wherein $R^1$ and $R^2$ are individually hydrogen or alkyl of 1 to 4 carbon atoms; $X^1$, $X^2$ and $X^3$ individually are hydrogen, alkyl of 1 to 4 carbon atoms; or the group

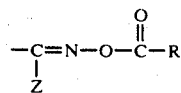

wherein Z is chloro, bromo, fluoro, iodo or nitro; R is alkyl of 1 to 6 carbon atoms optionally substituted with 1 to 13 fluoro, chloro or bromo atoms, alkenyl of 1 to 6 carbon atoms optionally substituted with 1 to 11 fluoro, chloro or bromo atoms, alkynyl of 3 to 6 carbon atoms optionally substituted with 1 to 9 fluoro, chloro or bromo atoms, alkoxy of 1 to 6 carbon atoms, alkoxyalkyl of 2 to 6 carbon atoms, phenyl, phenyl substituted with 1 to 2 of the same or different substituents selected from fluoro, chloro, bromo, iodo, alkyl of 1 to 4 carbon atoms, alkoxy of 1 to 4 carbon atoms or nitro, amino, alkylamino of 1 to 6 carbon atoms, dialkylamino of 2 to 6 carbon atoms; with the proviso that only one of $X^1$, $X^2$ or $X^3$ is

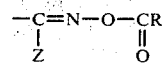

The pyridine salts of the invention are represented by the formula (Ia):

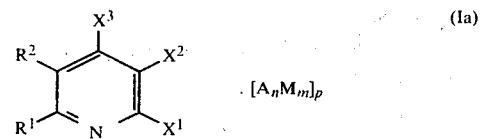

wherein $R^1$, $R^2$, $X^1$, $X^2$ and $X^3$ are defined above and A is hydrogen ion or a Group III metal cation, M is an inorganic anion and n and m are individually integers 1 through 6 and p is ½ or 1.

The pyridine N-oxides of the invention are represented by the formula (Ib):

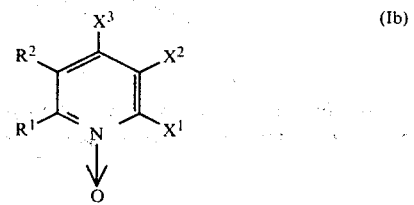

wherein $R^1$, $R^2$, $X^1$, $X^2$ and $X^3$ are defined above.

For pyridine compounds of the formula (I) representative $R^1$ and $R^2$ groups are hydrogen, methyl, ethyl, i-propyl, butyl.

Representative $X^1$, $X^2$ and $X^3$ alkyl groups are methyl, ethyl, i-propyl, n-propyl, n-butyl, i-butyl.

Representative Z groups are fluoro, chloro, bromo, iodo and nitro.

Representative R groups are methyl, ethyl, i-propyl, n-butyl, i-butyl, n-pentyl, methoxymethyl, ethoxymethyl, methoxyethyl, trichlorovinyl, 4-chloro-phenyl, 3,4-dichlorophenyl, 4-nitrophenyl, phenyl,2-fluorophenyl, methoxy, ethoxy, amino, methylamino, ethylamino, dimethylamino, diethylamino, ethylmethylamino, butylamino.

Representative $A_nM_m$ groups are HCl, $H_2SO_4$, $H_3PO_4$, $BF_3$, $AlCl_3$, $ZnCl_2$, $SnCl_4$. Preferably $A_nM_m$ is HCl. The particular p value depends on the nature of the $A_nM_m$ pyridine complex.

Representative pyridine N-oxides are compounds of formula (Ib) hwerein $R^1$, $R^2$, $X^2$ and $X^3$ are hydrogen and $X^1$ is

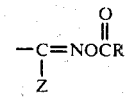

wherein Z is halo and R is p-chlorophenyl, methyl, trichlorovinyl, methoxymethyl, phenyl and 2,2,2-trichloro ethoxy.

Preferably $R^1$ and $R^2$ are hydrogen.

Preferably Z is halo. Most preferably Z is chloro.

Preferably R is trichlorovinyl, methoxy, methyl phenyl or substituted phenyl. Most preferably R is 4-nitrophenyl and 4-chlorophenyl.

Preferably the two X groups which are not the O-acyl aldoxime group are both hydrogen. Most preferably $X^1$ and $X^3$ are hydrogen.

The O-acyl (alpha-halo-formaldoxime)pyridines of the invention may be made according to the following scheme:

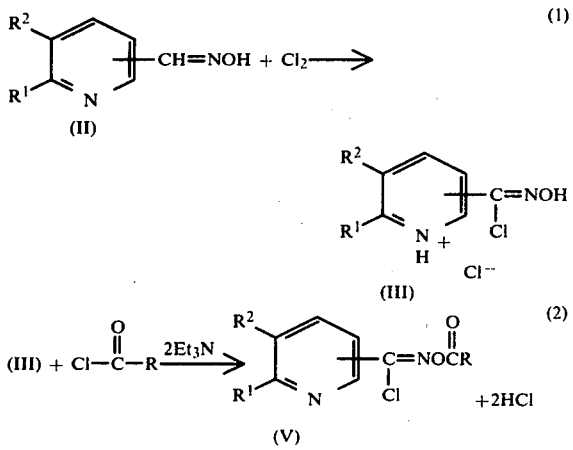

The pyridine N-oxides (Ib) of the invention can be made according to the following scheme:

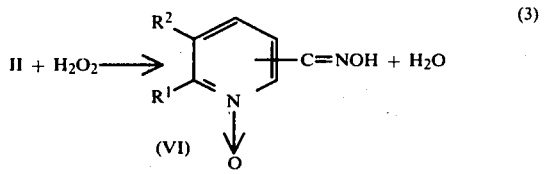

The N-oxide intermediate (VI) may then be halogenated as in reaction (1) and acylated as in reaction (2) to produce pyridine N-oxide products of the formula (Ib) wherein $X^1$, $X^2$ or $X^3$ is

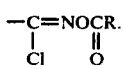

The O-acyl (alpha-nitro-formaldoxime)pyridines may be made according to the following scheme:

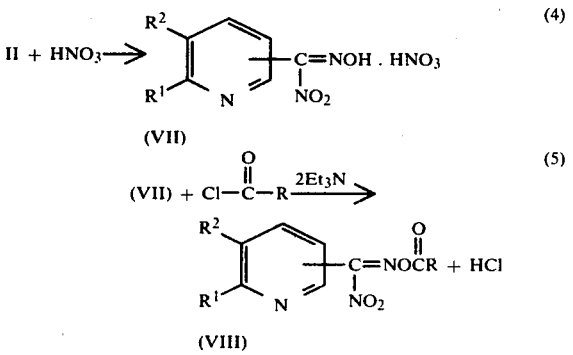

Reaction (1) is generally conducted by reacting the oxime (II) with an excess of gaseous chlorine in an inert solvent at a temperature of 0° to 50° C. The gaseous chlorine is usually bubbled through a solution containing the oxime (II) at about 0° C. until the exothermic reaction is complete, usually about 30 minutes. Stirring for several more hours at room temperature produces better yields.

Reactions (2) and (5) are generally conducted by reacting substantially equimolar amounts of the (alpha-haloformaldoxime)pyridinium hydrochloride (III) or alpha-nitro compound (VII) and the acid chloride (IV) in an inert organic solvent at a temperature of 0° to 50° C. A two-fold molar equivalent of a neutralizing base, such as triethylamine, is added. The reaction is usually complete after several hours. The pyridines of the formulas V and VIII may either be isolated as acid addition salts or subsequently converted to such salts of the formula (Ia) by conventional methods.

Reaction (3) may be carried out at room temperature in a suitable organic solvent, such as acetic acid.

Reaction (4) may be carried out by combining two molar equivalents of nitric acid with the formaldoxime pyridine (II) in a suitable solvent, such as methylene chloride, at room temperature.

The compounds of the invention have been found useful for controlling fungi, particularly plant fungal infections caused by leaf blights caused by organisms such as *Phytophthora infestans, Septoria apii, Alternaria solari, Plasmopora viticola, Fusarium moniloforma, Pythium ultimun* and *Aspergillus niger.*

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents, typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

EXAMPLE 1—Preparation of 2-(alpha-chloro-formaldoxime)-pyridinium hydrochloride 2-(Formaldoxime)-pyridine (50 g.) was dissolved in 500 ml methanol, stirred and cooled to ice bath temperature. Chlorine gas was bubbled through the solution over a period of 30 minutes, during which time the reaction was moderately exothermic causing the solution to reach 40°–45° C. After the chlorine addition was ceased, the solution was cooled again to ice bath temperature, stirred for 30 minutes. Stirring was continued for 3 hours at room temperature.

The solvent was stripped to yield a yellow solid, which was slurried in diethyl ether and air-dried to yield 58 g. of the title product.

EXAMPLE 2—Preparation of O-trichloro-acrylyl-4-(alpha-chloro-formaldoxime)-pyridine 4-(Alpha-chloro-formaldoxime)-pyridinium hydrochloride (4.9 g., prepared as in Example 1) and trichloroacrylyl chloride (5.2 g.) were mixed in 75 ml. methylene chloride and cooled to ice bath temperature. Triethylamine (5.7 g.) was added dropwise and stirring was continued at room temperature for 3 hours.

The mixture was diluted with 250 ml. benzene/methylene chloride, washed with water, dried (MgSO$_4$ and silica), filtered. The solvent was stripped to yield a tan solid, which was crystallized in hexene to yield 4.5 g. of the title product.

EXAMPLE 3—Tomato Late Blight

Compounds of the invention were tested for the control of the Tomato Late Blight organism *Phytophthora infestans conidia*. Six- to seven-week-old tomato (variety Bonny Best) seedlings were used. The tomato plants were sprayed with a 250-ppm solution of the test compound in acetone, water and a small amount of a non-ionic emulsifier. The sprayed plants were then inoculated one day later with the organism, placed in an environmental chamber and incubated at 19°–20° C. and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The compounds giving effective control at the test concentration are tabulated in Table I.

EXAMPLE 4—Tomato Early Blight

Compounds of the invention were tested for the control of the Tomato Early Blight organism, *Alternaria solani conidia*. Tomato (variety Bonny Best) seedlings of 6 to 7 weeks old were used. The tomato plans were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds giving effective control at the test concentration are tabulated in Table I.

EXAMPLE 5—Celery Late Blight

Compounds of the invention were tested for the control of Celery Late Blight using celery (Utah) plants 12 to 14 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 19°–20° C. in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants. The compounds giving effective control at the test concentrations are reported in Table I.

EXAMPLE 6—Mycelial Inibition

A number of the compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by covering the paper with a potato dextrose broth culture of mycelial suspension. The inoculated papers were then placed on potato dextrose agar plates and sprayed by means of a micro sprayer with the fungicidal solution. The treated paper strips were incubated at 25° C. and data is taken after 24 hours. Fungicidal activities are measured by a zone of inhibited mycelial growth from the center of the paper strip. The effectiveness of the compounds tested by fungicidal activity is reported in Table I in terms of percent control of the fungus relative to the control standard DIFOLATAN.

EXAMPLE 7—Grape Downy Mildew Control

The compounds of the invention were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a 250 ppm solution of the test compound in acetone. The sprayed leaves were dried, inoculated with a spore suspension of the organism, placed in a humid environmental chamber and incubated at 18°–20° C. and about 100% relative humidity. Seven to nine days after inoculation, the amount of disease control was determined. The percent disease control provided by a given test compound was based on the percent disease reduction relative to untreated check plants. The results are tabulated in Table I.

TABLE A

Compounds of the Formula $$\underset{R^1 \diagdown N \diagup X^1}{\overset{X^3 \diagdown \diagup X^2}{\bigcirc}}$$

| No. | $X^1$ | $X^2$ | $X^3$ | $R^1$ | mp °C. | C Cal. | C Fd. | H Cal. | H Fd. | N Cal. | N Fd. |
|-----|-------|-------|-------|-------|--------|--------|-------|--------|-------|--------|-------|
| 1 | C(=NOCC(=CCl$_2$)Cl)Cl, O | H | H | H | 83–85 | 34.4 | 34.54 | 1.3 | 1.36 | 8.9 | 10.38 |
| 2 | C(=NOC(=O)-C$_6$H$_4$-Cl)Cl | H | H | H | 176–177 | 52.9 | 52.95 | 2.7 | 2.81 | 9.5 | 10.08 |
| 3 | C(=NOC(=O)NHCH$_3$)Cl | H | H | H | 158–159 | 44.97 | 45.24 | 3.5 | 3.94 | 19.7 | 20.19 |
| 4 | H | H | C(=NOCC(=CCl$_2$)Cl)Cl, O | H | 70–72 | 34.4 | 34.93 | 1.3 | 1.46 | 8.9 | 9.6 |
| 5 | C(=NOC(=O)NHCH$_3$)Br | H | H | H | 145–148 | 37.2 | 37.65 | 3.1 | 3.2 | 16.3 | 16.91 |
| 6 | H | H | C(=NOC(=O)-C$_6$H$_3$-Cl$_2$)Cl | H | 124–125 | 47.4 | 48.44 | 2.1 | 2.3 | 8.5 | 9.19 |
| 7 | H | H | C(=NOCCH$_2$OCH$_3$)Cl, O | H | 70–72 | 47.3 | 48.07 | 4.0 | 4.13 | 12.2 | 12.85 |
| 8 | H | C(=NOCC(=CCl$_2$)Cl)Cl, O | H | H | 88–90 | 34.4 | 36.59 | 1.3 | 1.47 | 8.9 | 9.83 |
| 9 | H | C(=NOCCH$_2$OCH$_3$)Cl, O | H | H | 55–56 | 47.3 | 48.05 | 4.0 | 4.05 | 12.2 | 13.21 |
| 10 | H | C(=NOC(=O)-C$_6$H$_4$-Cl)Cl | H | H | 111–113 | 52.9 | 53.68 | 2.7 | 2.88 | 9.5 | 9.94 |

TABLE A-continued

Compounds of the Formula

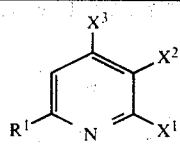

| No. | X¹ | X² | X³ | R¹ | mp °C. | C Cal. | C Fd. | H Cal. | H Fd. | N Cal. | N Fd. |
|---|---|---|---|---|---|---|---|---|---|---|---|
| 11 | C(Cl)=NOCCH₂OCH₃ (with C=O) | H | H | H | 57 | 47.3 | 46.87 | 4.0 | 4.01 | 12.2 | 12.20 |
| 12 | C(Cl)=NOC(=O)C₆H₅ | H | H | H | 130–131 | 59.9 | 59.09 | 3.5 | 3.59 | 10.7 | 10.87 |
| 13 | C(Cl)=NOC(=O)C₆H₄-NO₂ | H | H | H | 212–213 | 51.1 | 51.38 | 2.6 | 2.73 | 13.7 | 14.6 |
| 14 | C(Cl)=NOC(=O)C₆H₄-F | H | H | H | 133–135 | 56.0 | 56.08 | 2.9 | 3.14 | 10.0 | 11.27 |
| 15 | C(Cl)=NOCSC₂H₅ (with C=O) | H | H | H | 35–37 | 44.2 | 44.92 | 3.7 | 3.8 | 11.4 | 11.94 |
| 16 | H | C(Cl)=NOC(=O)C₆H₅ | H | H | 105 | 59.9 | 59.96 | 3.5 | 3.56 | 10.7 | 11.21 |
| 17 | H | H | C(Cl)=NOC(=O)C₆H₅ | H | 131–132 | 59.9 | 59.64 | 3.5 | 3.47 | 10.7 | 10.82 |
| 18 | H | H | C(Cl)=NOC(=O)C₆H₄-NO₂ | H | 188–190 | 51.1 | 50.88 | 2.6 | 3.1 | 13.7 | 13.93 |
| 19 | C(Cl)=NOCOCH₃ | H | H | H | 92–96 | 44.8 | 45.74 | 3.3 | 3.3 | 13.1 | 13.75 |
| 20 | C(Cl)=NOCCH₂OCH₃ (with C=O) | H | H | CH₃ | 46 | 49.5 | 49.07 | 4.6 | 4.65 | 11.5 | 11.39 |
| 21 | C(Cl)=NOCCH₂OCH₃ (with C=O) | H | H | CH₃ | 119–120 | 61.2 | 61.21 | 4.0 | 3.92 | 10.2 | 10.22 |
| 22 | C(Cl)=NOCC(Cl)=CCl₂ (with C=O) | H | H | CH₃ | 76–77 | 36.6 | 36.37 | 1.8 | 1.85 | 8.5 | 8.49 |
| 23 | H | H | C(Cl)=NOC(=O)C₆H₄-Cl | H | 150–151 | 52.9 | 52.73 | 2.7 | 2.85 | 9.5 | 9.56 |
| 24 | H | H | C(Cl)=NOC(=O)C₆H₃Cl₂ | H | 169–170 | 47.4 | 47.2 | 2.1 | 2.23 | 8.5 | 8.69 |
| 25 | C(NO₂)=NOCCH₃ (with C=O) | H | H | H | 90–92 | 45.9 | 44.24 | 3.4 | 3.86 | 20.1 | 20.34 |

TABLE A-continued

Compounds of the Formula

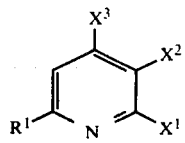

| No. | X$^1$ | X$^2$ | X$^3$ | R$^1$ | mp °C. | C Cal. | C Fd. | H Cal. | H Fd. | N Cal. | N Fd. |
|---|---|---|---|---|---|---|---|---|---|---|---|
| 26 | C(=NO₂)C(=O)O-C₆H₄-Cl | H | H | H | 145–157 | 51.1 | 50.68 | 2.6 | 2.58 | 13.7 | 14.35 |
| 27 | C(=NO₂)C(=O)O-C₆H₅ | H | H | H | 104–105 | 57.6 | 57.0 | 3.3 | 3.46 | 15.5 | 15.72 |
| 28 | C(=NO₂)C(=O)OC(Cl)=CCl₂ | H | H | H | 80–81 | 33.3 | 33.71 | 1.24 | 1.35 | 12.9 | 13.50 |
| 29 | C(=NO₂)C(=O)OCH₃ | H | H | CH₃ | 111–113 | 48.3 | 48.38 | 4.1 | 4.16 | 18.8 | 19.13 |
| 30 | C(=NO₂)C(=O)O-C₆H₅ | H | H | CH₃ | 118–121 | 58.9 | 52.69 | 3.9 | 3.9 | 14.7 | 13.88 |
| 31 | C(=NO₂)C(=O)OC(Cl)=CCl₂ | H | H | CH₃ | 115–118 | 35.5 | 36.17 | 1.8 | 2.1 | 12.4 | 12.78 |
| 32 | H | C(Cl)=NOC(=O)-C₆H₄-NO₂ | H | H | 160–163 | 51.1 | 50.62 | 2.6 | 2.73 | 13.7 | 14.27 |

TABLE B

Compounds Of The Formula

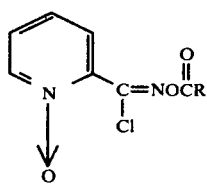

| No. | R | mp °C. | C Cal. | C Fd. | H Cal. | H Fd. | N Cal. | N Fd. |
|---|---|---|---|---|---|---|---|---|
| 33 | p-Cl-phenyl | 188–190 | 50.2 | 50.3 | 2.6 | 2.72 | 9.0 | 8.96 |
| 33A | phenyl | 185–188 | 50.4 | 56.35 | 3.3 | 3.32 | 10.1 | 10.24 |
| 34 | CH₃CCl= | 117 | 44.8 | 44.68 | 3.3 | 3.27 | 13.0 | 13.22 |

TABLE B-continued

Compounds Of The Formula

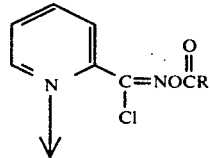

| No. | R | mp °C. | C Cal. | C Fd. | H Cal. | H Fd. | N Cal. | N Fd. |
|---|---|---|---|---|---|---|---|---|
| 35 | CCl₂CH₂- | 107–109 | 30.8 | 30.22 | 1.2 | 1.17 | 8.5 | 7.13 |
| 36 | OCH₃ | 100–101 | 44.2 | 44.46 | 3.7 | 3.8 | 11.4 | 11.59 |
| 37 | CH₂CCl₃ | 126–127 | 31.1 | 31.33 | 1.7 | 1.81 | 8.0 | 8.32 |

TABLE C

Compounds of the Formula $$\underset{N}{\text{pyridine}}\text{ with } X^3 \text{ and } X^2 \cdot [A_nM_m]_p$$

| No. | $X^2$ | $X^3$ | AnMm | p | mp °C. | C Cal. | C Fd. | H Cal. | H Fd. | N Cal. | N Fd. |
|---|---|---|---|---|---|---|---|---|---|---|---|
| 4S | H | C(Cl)=NOCC(=O)C=CCl₂ with Cl | HCl | ½ | 144–162 | 32.5 | 31.04 | 1.35 | 1.46 | 8.4 | 8.66 |
| 38 | C(Cl)=NOCOCH₃ | H | HCl | 1 | 145–147 | 38.27 | 39.76 | 3.21 | 3.31 | 11.16 | 11.73 |
| 32S | C(Cl)=NOC(=O)–C₆H₄–NO₂ | H | HCl | 1 | 157 | 45.63 | 44.29 | 2.65 | 2.94 | 12.25 | 11.96 |
| 10S | C(Cl)=NOC(=O)–C₆H₄–Cl | H | HCl | 1 | 137–143 | 47.08 | 48.45 | 2.74 | 2.88 | 8.45 | 8.59 |

TABLE I

| | | | | FUNGICIDAL ACTIVITY | | | | | | |
|---|---|---|---|---|---|---|---|---|---|---|
| No. | P | R | F | B | A | G | TL | C | TE | BP |
| 1 | 0 | — | 0 | 0 | 88 | 100ᵃ | 100 | 73 | 44 | 0 |
| 2 | 0 | — | 0 | 0 | 61 | 0ᵃ | 100 | 100 | 63 | 14 |
| 3 | — | 0 | 0 | — | 0 | — | — | 99 | 0 | 11 |
| 4 | 88 | — | 68 | 30 | 41 | 98ᵃ | 100 | 63 | 0 | 100 |
| 5 | 0 | — | 0 | 0 | 0 | — | 100 | 100 | 68 | 0 |
| 6 | 0 | 17 | 45 | 0 | 33 | — | — | 98 | — | 0 |
| 7 | 0 | 17 | 45 | 13 | 33 | — | — | 88 | — | 84 |
| 8 | 25 | 63 | 89 | 0 | 110 | — | 100 | 68 | 0 | 95 |
| 9 | 0 | 94 | 72 | 0 | 106 | — | 86 | 89 | 0 | 63 |
| 10 | 23 | 47 | 72 | 25 | 94 | 93ᵃ | 100 | 100 | 63 | 23 |
| 11 | 88 | 0 | 105 | 49 | 50 | — | 0 | 0 | 0 | 0 |
| 12 | 69 | 17 | 78 | 34 | 63 | — | 100 | 98 | 0 | 23 |
| 13 | — | 0 | 0 | 0 | 0 | — | 100 | 93 | 0 | 0 |
| 14 | — | 33 | 104 | 20 | 46 | — | 100 | 99 | 0 | 0 |
| 15 | 0 | 0 | 42 | 24 | 45 | — | 0 | 50 | 0 | 0 |
| 16 | 26 | 14 | 56 | 43 | 42 | — | 100 | 85 | 0 | 21 |
| 17 | 48 | 31 | 60 | 90 | 23 | — | 85 | 97 | 0 | 81 |
| 18 | 0 | 0 | 61 | 0 | 35 | — | 73 | 95 | 0 | 0 |
| 19 | 0 | 28 | 45 | 100 | 43 | — | 50 | 0 | 0 | 0 |
| 20 | 100 | 15 | 78 | 40 | 54 | — | 0 | 0 | 0 | 13 |
| 21 | 0 | 0 | 48 | 21 | 50 | — | 94 | 97 | 0 | 0 |
| 22 | 0 | 0 | 53 | 26 | 51 | — | 81 | 100 | 0 | 0 |
| 23 | 0 | 0 | 36 | 0 | 20 | — | 100 | 100 | 23 | 0 |
| 24 | 0 | 0 | 0 | 0 | 0 | — | 100 | 97 | 0 | 81 |
| 25 | — | 13 | 81 | 33 | 74 | — | 0 | 0 | 0 | 0 |
| 26 | 0 | — | 0 | 0 | 0 | — | 100 | 91 | 75 | 0 |
| 27 | 0 | 0 | 0 | 0 | 0 | — | 100 | 99 | 27 | 0 |
| 28 | 0 | 23 | 50 | 0 | 0 | — | 23 | 50 | 0 | 0 |
| 29 | 0 | 0 | 73 | 19 | 71 | — | 0 | 27 | 0 | 0 |
| 30 | 0 | 0 | 0 | 0 | 0 | — | 56 | 89 | 0 | 0 |
| 31 | 0 | 0 | 0 | 0 | 80 | — | 100 | 100 | 0 | 0 |
| 32 | 0 | 13 | 62 | 25 | 19 | — | 100 | 99 | — | 13 |
| 33 | 0 | 24 | 27 | 0 | 33 | 14 | 13 | 14 | 50 | 0 |
| 33A | 0 | 0 | 0 | 0 | 0 | 23 | 0 | 64 | 44 | 0 |
| 34 | 0 | 0 | 0 | 0 | 0 | 0 | 0 | 35 | 0 | 0 |
| 35 | 0 | 0 | 0 | 0 | 0 | 0 | 0 | 35 | 0 | 0 |
| 36 | 0 | 0 | 0 | 0 | 0 | 0 | 0 | 18 | 0 | 0 |
| 37 | 0 | 0 | 0 | 0 | 0 | 0 | 0 | 35 | 0 | 0 |
| 4S | — | 80 | 48 | 27 | 24 | — | 89 | 76 | 0 | 0 |
| 38 | 46 | 50 | 47 | 31 | 54 | 96 | 18 | 0 | 0 | 0 |
| 32S | 29 | 31 | 36 | 14 | 22 | 100 | 99 | 85 | 79 | 23 |

| TABLE I-continued | | | | | | | | | |
|---|---|---|---|---|---|---|---|---|---|
| | | | FUNGICIDAL ACTIVITY | | | | | | |
| No. | P | R | F | B | A | G | TL | C | TE | BP |
| 10S | 50 | 41 | 49 | 16 | 25 | 100 | 98 | 85 | 92 | 23 |

*a*100 ppm
P* = *Pythium ultimum*
R = *Rhizoctonia solani*
F = *Fusarium moniloforma*
B = *Botrytis cinerea*
A = *Aspergillus niger*
G** = Grape downy mildew (*Plasmopara viticola*)
TL = Tomato late blight (*Phytophthora infestans*)
C = Celery late blight (*Septoria apii*)
TE = Tomato early blight (*Alternaria solani*)
BP = Bean powdery mildew (*Erysiphe polygoni*)
*P, R, F, B and A were tests against the standard DIFOLATAN. Therefore, results greater than 100% are possible when activity is better than the standard.
**G, TL, C, TE and BP were tests against untreated control plants. Therefore, 100% is the maximum activity possible.

What is claimed is:

1. A compound of the formula

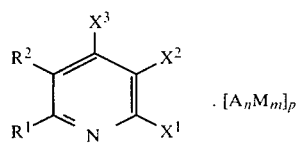 . [A$_n$M$_m$]$_p$ wherein R$^1$ and R$^2$ are individually hydrogen or alkyl of 1 to 4 carbon atoms; and X$^1$, X$^2$ and X$^3$ individually are hydrogen, alkyl of 1 to 4 carbon atoms, or

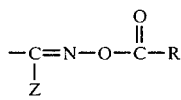

wherein R is alkyl of 1 to 6 carbon atoms optionally substituted with 1 to 13 fluoro, chloro or bromo atoms, alkenyl of 1 to 6 carbon atoms optionally substituted with 1 to 11 fluoro, chloro or bromo atoms, alkynyl of 3 to 6 carbon atoms optionally substituted with 1 to 9 fluoro, chloro or bromo atoms, alkoxyalkyl of 2 to 6 carbon atoms, phenyl, phenyl substituted with 1 to 2 of the same or different substituents selected from fluoro, chloro, bromo, iodo, alkyl of 1 to 4 carbon atoms, alkoxy of 1 to 4 carbon atoms or nitro, and Z is chloro, bromo, fluoro, iodo or nitro; A is hydrogen ion or a Group III metal cation; M is an inorganic anion; n and m are individually integers 1 through 6; and p is 0, ½ or 1; with the proviso that two of X$^1$, X$^2$ and X$^3$ are hydrogen or alkyl as defined above and one of X$^1$, X$^2$ or X$^3$ is

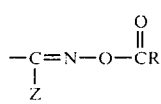

2. A compound of the formula

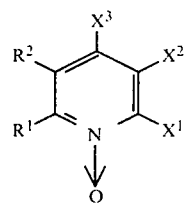

wherein R$^1$ and R$^2$ are individually hydrogen or alkyl of 1 to 4 carbon atoms; and X$^1$, X$^2$ and X$^3$ individually are hydrogen, alkyl of 1 to 4 carbon atoms, or

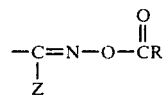

wherein R is alkyl of 1 to 6 carbon atoms optionally substituted with 1 to 13 fluoro, chloro or bromo atoms, alkenyl of 1 to 6 carbon atoms optionally substituted with 1 to 11 fluoro, chloro or bromo atoms, alkynyl of 3 to 6 carbon atoms optionally substituted with 1 to 9 fluoro, chloro or bromo atoms, alkoxyalkyl of 2 to 6 carbon atoms, phenyl substituted with 1 to 2 of the same or different substituents selected from fluoro, chloro, bromo, iodo, alkyl of 1 to 4 carbon atoms, alkoxy of 1 to 4 carbon atoms or nitro, and Z is chloro, bromo, fluoro, iodo or nitro; with the proviso that two of X$^1$, X$^2$ and X$^3$ are hydrogen or alkyl as defined above and one of X$^1$, X$^2$ or X$^3$ is

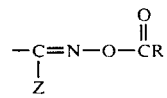

3. A compound according to claim 1 wherein R$^1$ and R$^2$ are both hydrogen.

4. A compound according to claim 3 wherein Z is chloro or nitro.

5. A compound according to claim 4 wherein R is halovinyl of 1 to 3 fluoro, chloro or bromo atoms.

6. A compound according to claim 4 wherein R is phenyl or phenyl substituted with 1 or 2 of the same or different substituents selected from fluoro, chloro, bromo, iodo, alkyl of 1 to 4 carbon atoms, alkoxy of 1 to 4 carbon atoms or nitro.

7. The compound according to claim 6 wherein Z is chloro, R is 4-chlorophenyl, $X^1$ and $X^3$ are hydrogen, p is 0 or 1 and $A_nM_m$ is HCl.

8. The compound according to claim 6 wherein Z is chloro, R is 4-nitrophenyl, $X^1$ and $X^3$ are hydrogen, p is 0 or 1 and $A_nM_m$ is HCl.

9. The compound according to claim 5 wherein Z is chloro, R is trichlorovinyl, $X^1$ and $X^3$ are hydrogen, and p is 0.

10. A method for the control of fungi which comprises contacting said fungi or their habitats with a fungicidally effective amount of a compound of the formula defined in claim 1.

11. A method for controlling the growth of *Phytophthora infestans* fungi which comprises applying to said fungi or their habitats a fungicidally effective amount of a compound of the formula defined in claim 1.

12. A method for controlling the growth of *Plasmopara viticola* fungi which comprises applying to said fungi or their habitats a fungicidally effective amount of a compound of the formula defined in claim 1.

13. A fungicidal composition comprising a biologically inert carrier and a fungicidally effective amount of a compound of the formula defined in claim 1.

14. A method for the control of fungi which comprises contacting said fungi or their habitats with a fungicidally effective amount of a compound of the formula defined in claim 2.

15. A fungicidal composition comprising a biologically inert carrier and a fungicidally effective amount of a compound defined in claim 2.

* * * * *

UNITED STATES PATENT AND TRADEMARK OFFICE
CERTIFICATE OF CORRECTION

PATENT NO. : 4,244,959

DATED : January 13, 1981

INVENTOR(S) : Francis J. Freenor, III

It is certified that error appears in the above—identified patent and that said Letters Patent are hereby corrected as shown below:

Col. 8, line 14 "18-20°" should read --18-22°C--.

Signed and Sealed this

Twenty-fifth Day of August 1981

[SEAL]

Attest:

Attesting Officer

GERALD J. MOSSINGHOFF

Commissioner of Patents and Trademarks